(12) United States Patent
Fujii et al.

(10) Patent No.: US 7,169,762 B2
(45) Date of Patent: Jan. 30, 2007

(54) SUBSTANCE HAVING PHYSIOLOGICAL PROPERTY, METHOD FOR PRODUCING THE SAME AND USES THEREOF

(75) Inventors: Hajime Fujii, Hokkaido (JP); Takashi Nakagawa, Hokkaido (JP); Buxiang Sun, Hokkaido (JP)

(73) Assignee: Amino Up Chemical Co., Ltd. (JP)

( * ) Notice: Subject to any disclaimer, the term of this patent is extended or adjusted under 35 U.S.C. 154(b) by 38 days.

(21) Appl. No.: 10/975,415

(22) Filed: Oct. 29, 2004

(65) Prior Publication Data

US 2005/0143341 A1 Jun. 30, 2005

Related U.S. Application Data

(62) Division of application No. 10/181,252, filed as application No. PCT/JP01/06860 on Aug. 9, 2001, now Pat. No. 6,831,067.

(30) Foreign Application Priority Data

Feb. 8, 2001 (JP) .............................. 2001-31852

(51) Int. Cl.
*A61K 31/70* (2006.01)
*A61K 31/7048* (2006.01)
*A61K 31/715* (2006.01)
*C07H 17/04* (2006.01)

(52) U.S. Cl. .................... 514/25; 514/54; 536/4.1; 536/123.1; 536/124; 424/439; 435/101

(58) Field of Classification Search .............. 514/25, 514/54; 536/4.1, 123.1, 124; 435/72, 101; 424/439
See application file for complete search history.

(56) References Cited

U.S. PATENT DOCUMENTS

| 3,015,654 A | 1/1962 | Hodge et al. | |
| 4,629,627 A | 12/1986 | Iizuka | |
| 5,560,914 A * | 10/1996 | Ghoneum et al. | 424/195.15 |
| 5,756,318 A | 5/1998 | Kosuna | |

FOREIGN PATENT DOCUMENTS

| JP | 54-109960 | 8/1979 |
| JP | 62-36009 | 8/1987 |
| JP | 06 135987 A | 5/1994 |
| JP | 6-88909 | 11/1994 |
| JP | 8-259602 | 10/1996 |
| JP | 11-158080 | 6/1999 |
| JP | 2001-106637 | 4/2001 |
| WO | WO 01/44488 | 6/2001 |

OTHER PUBLICATIONS

Pellegrino, L., et al., "Formation of protein bound lysine-derived galactosyl and glucosyl pyrroles in heated model systems," Nahrung, 2000, 44(3):193-200.
Kramhoeller, B., et al., "Maillard reactions of lactose and maltose," Journal of Agricultural and Food Chemistry, 1993, 41(3):347-51.
Kramhoeller, B.., et al., "HPLC separation of some characteristics components in reaction mixtures of disaccharides with amines—model systems for milk and cereal products," Zeitschrift fuer Lebensmittel-Untersuchung und -Forschung, 1992, 194(5):431-3.
Estendorfer, S., et al., "Formation of 4.5-dihydroxy-2-.alpha.-D-glucopyranosyloxy-5-methyl-2-cyclopenten-1-one in the Maillard reaction of maltose," Tetrahedron, 1990, 46(16):5617-20.
Goodwin, J.C., et al., "Amine-catalyzed transformation of enolic nonenzymic browning products, isomaltol glycopyranosides into 1,6-anhydro-.beta.-D-hexopyranoses," Carbohydrate Research, 1985, 143:61-8.
Ledl, F., "Formation of amino reductones from disaccharides," Zeitschrift fuer Lebensmittel-Untersuchung und -Forschung, 1984, 179(5):381-4.
Goodwin, J.C., "Isolation of 3-O-.alpha.-D-gluco- and 3-O-.beta.-D-galacto-pyranosyloxy-2-furyl methyl ketones from nonenzymic browning of maltose and lactose with secondary amino acids," Carbohydrate Research, 1983, 115(1):281-7.
Bartulin, J. et al., "Syntheses of 2-Acetyl-3-hydroxy-1-*n*-propylpyrrole from Isomaltol and 1-*n*Alkyl-3-hydroxy-2-methyl-4-pyridones from Maltol," J. Heterocyclic Chem., 29:1017 (Jul. 1992).
Goodwin (Carbohydrate Research 1983), 115 91, 281-7.

* cited by examiner

Primary Examiner—Shaojia Anna Jiang
Assistant Examiner—Michael C. Henry
(74) Attorney, Agent, or Firm—Finnegan, Henderson, Farabow, Garrett & Dunner, LLP (57) ABSTRACT

A glucoside containing isomaltol represented by formula (I):

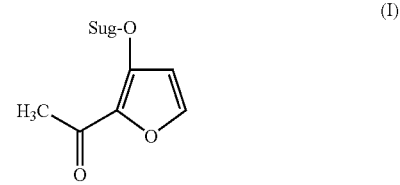

(I)

(wherein Sug represents a glucose residue or a sugar linkage composed of two or more glucose units) as an aglycon, a physiologically active substance containing the glucoside having human cytokine inducing ability increasing activity, a method for producing it, and food, medicine and feedstuff containing the substance.

2 Claims, 2 Drawing Sheets

Fig. 5

SUBSTANCE HAVING PHYSIOLOGICAL PROPERTY, METHOD FOR PRODUCING THE SAME AND USES THEREOF

This is a division of application Ser. No. 10/181,252, filed Jul. 16, 2002, now U.S. Pat. No. 6,831,067 which is a 371 of PCT/JP01/06860, filed Aug. 9, 2001, all of which are incorporated herein by reference.

TECHNICAL FIELD

The present invention relates to novel glycoside compounds, to physiologically active substance containing them as active ingredients, to a method for producing them, and to their uses. More particularly, the present invention relates to glucosides containing isomaltol as an aglycon, to physiologically active substances containing the glucosides as active ingredients, to a method for producing them and to their uses.

BACKGROUND ART

It is known that cultures of basidiomycete have properties of BRM (Biological Response Modifiers) such as immunopotentiation, immunological activation, or macrophage activation.

Also the present inventors have filed a patent application on an agent for recovering productivity of cytokines such as human monocyte interferon gamma (IFN-γ), or interleukin 12 (IL-12) using a culture of basidiomycete (a fungus belonging to Basidiomycetes) (Japanese Patent Application No. Hei 11-283223).

The physiological activities contained in such a culture of basidiomycete have been disclosed in "Water-soluble lignin" (Examined Japanese Patent Publication No. Hei 6-88909), "Complex of cyctokinin based active substance composed mainly of polysaccharide and zeatin-related substance" (Examined Japanese Patent Publication No. Sho 62-36009), novel polysaccharide substances (Japanese Patent Application Laid-open No. Hei 8-259602) and so forth. As shown in these applications, basidiomycete cultures may contain several types of physiologically active substances. However, none of the physiologically active substance has been identified by the structure in such a manner that the existence thereof can be unambiguously confirmed by instrumental analysis, in particular a spectroscopic method (including nuclear magnetic resonance or the like).

In conventional methods, plant tissue materials have been used, so that the cultures contain various types of organic substances. Furthermore, little information on the structure of target compounds is available. This makes it difficult to distinguish the fraction containing the target substance by instrumental analysis even if separations means such as column chromatography is used. Therefore, it has been difficult to efficiently isolate and produce the component having excellent physiological activity.

OBJECT OF THE INVENTION

It is an object of the present invention to elucidate the structure of main substances from among the components that bring about the physiological activity contained in the basidiomycete cultures to which the present inventors have paid attention for a long time, to specify conditions for producing the substance efficiently, and to provide uses such as food, medicine and feedstuff utilizing the physiological activity of the substance.

DISCLOSURE OF THE INVENTION

The present inventors have made extensive studies with a view to solving the above-mentioned problems. As a result, they have found out that reacting a culture solution obtained by preliminarily culturing a basidiomycete with a reaction mixture obtained by reacting bran extracts with an enzyme gives rise to a substance having an increased physiological activity. This is in contrast to the conventional culture method of basidiomycete in a medium containing a plant tissue material. Also, the present inventors have identified the substance. The present invention has been achieved based on the discoveries.

That is, the present invention relates to novel substances having a physiological activity, method for producing them, and their use as set forth below.

1. A glucoside containing isomaltol represented by formula (I):

(wherein Sug represents a glucose residue or a sugar linkage composed of two or more glucose units) as an aglycon.

2. A glucoside according to 1 above, represented by formula (II):

(wherein n is 0 or an integer of 1 or more).

3. A glucoside according to 2 above, wherein n is 1 to 20.

4. A glucoside according to any one of 1 to 3 above, wherein the glucoside is obtained by reacting a culture solution obtained by culturing a basidiomycete with a reaction mixture of a rice bran extracts solution and an enzyme, and then isolating the glucoside by column chromatography.

5. A 2-acetyl-3-hydroxyfuran-3-O-α-D-glucopyranoside represented by formula (III):

(III)

which corresponds to the formula (II) in which n is 0.
6. A physiologically active substance comprising a glucoside according to 1 or 2 above as an active ingredient.
7. The substance having a physiologically activity according to 6 above, wherein the physiological activity increases human cytokine inducing ability.
8. The substance having a physiological activity according to 7 above, wherein the cytokine is tumor cell necrosis factor (TNF-α)
9. The substance having a physiological activity according to 7 above, wherein the cytokine is interferon-gamma (IFN-γ)
10. The substance having a physiological activity according to 7 above, wherein the cytokine is interleukin-2 (IL-2).
11. A method for producing a glucoside represented by formula (I):

(I)

(wherein symbols have the same meanings as defined in 1 above) having a physiological activity, comprising the step of reacting a culture solution obtained by culturing a basidiomycete with a reaction mixture obtained by reaction between a rice bran extracts solution and an enzyme, and isolating the glucoside.
12. A method for producing a glucoside represented by formula (I) in 1 above, having a physiological activity, comprising the steps of reacting a culture solution obtained by culturing a basidiomycete with a reaction mixture obtained between a rice bran extracts solution and an enzyme, and isolating the glucoside by column chromatography using as an index a component showing (1) a peak attributable to methyl hydrogen of methyl ketone by $^1$H-NMR spectrum and a peak attributable to hydrogen atoms at the 4,5-positions of a 2,3-di-substituted furan ring characteristic of AB system, and (2) 6 peaks attributable to glucopyranose and 6 peaks attributable to isomaltol by $^{13}$C-NMR.
13. A food containing a substance having a physiological activity according to any one of 6 to 10 above.
14. A medicine containing a substance having a physiological activity according to any one of 6 to 10 above.
15. A feedstuff containing a substance having a physiological activity according to any one of 6 to 10 above.

DETAILED DESCRIPTION OF THE INVENTION

Hereinafter, the present invention will be illustrated in detail.

(A) Glucoside Compounds

The glucoside compounds of the present invention are novel glucosides having isomaltol as an aglycon, represented by formula (I)

(I)

obtained by reacting a culture solution obtained by culturing a basidiomycete with a reaction mixture obtained by a bran extract and an enzyme (hereinafter sometimes abbreviated as "rice bran extracts solution-enzyme reaction mixture") and isolating by column chromatography (details will be described hereinbelow).

The isomaltol is a substance represented by formula:

which is used as a component of a perfume.

As for the glycoside having isomaltol as an aglycon, there is an example that refers to galactoside (glycoside of which the sugar moiety is galactose (J. Bartulin et al., J. Heterocycle Chem., 29, 1017 (1992), "Syntheses of 2-Acetyl-3-hydroxy-1-n-propylpyrrole from Isomaltol and 1-n-Alkyl-3-hydroxy-2-methyl-4-pyridones from Maltol"). However, no report has been made on glucoside (which is a glycoside with the sugar moiety composed of glucose units), and functions of such glucoside are unknown.

In the case where Sug contains 2 or more glucose units, the length of sugar linkage is not particularly limited. According to the method of the present invention, mixtures of glucosides with n varying from 1 to 20 occupy about 10% of the solid reaction product. The sugar linkage (Sug) may contain α (1→46) bond or other bonds as a part thereof. Also it may contain branched chain. However, it is a linear sugar linkage mainly comprising α (1→4) bonds.

A typical structure of novel glycoside compound is represented by formula (II):

(wherein n is 0 or an integer of 1 or more).

For example, novel 2-acetyl-3-hydroxyfuran 3-O-α-D-glucopyranoside represented by formula (III):

having one glucose unit, which corresponds to the formula (II) above in which n is 0, can be isolated by the method of the present invention or prepared by chemical synthesis.

(B) Physiologically Active Substance

The novel glucoside compound of the present invention mentioned above has excellent physiological activities.

The physiological activities include immunopotentiation/activation, macrophage activation and the like properties, in particular improvement of cytokine inducing ability of human cells.

Examples of the cytokine induced by the physiological active substance of the present invention include tumor necrosis factor (TNF-α), interferon gamma (IFN-γ), interleukin-2 (IL-2) and so forth. However, it is not limited to these.

The tumor necrosis factor TNF-α is a protein that has activity of killing tumor cells and is a cytokine produced systemically or locally in response to infection, wound or immunological induction. Interferon (IFN) is an antiviral protein produced upon receiving stimulation by virus or nucleic acid and secreted outside cells. It is known that interferons exhibit not only antiviral activity but also various activities such as antitumor activity and activation of immune systems. IFN-γ is produced by T cells and so forth. Interleukin-2 (IL-2) has effects of degeneration or eradication of tumors.

(C) Production and Isolation Methods

The compounds represented by the formula (I) above having the physiological activity as described above are novel substances that have not been reported yet. The present inventors have confirmed that the compounds are not present in cultures of basidiomycete or in the rice bran extracts solution-enzyme reaction mixture, and that they are not produced when rice bran is added to the medium from the beginning of culture. They also confirmed that the compounds could be produced only in a solution obtained by reacting the culture of a basidiomycete with the rice bran extracts solution-enzyme reaction mixture.

Conventionally, cultivation of a basidiomycete has been performed in media containing plant tissue materials. However, it is beyond expectation that reaction between a culture solution obtained by preliminarily culturing basidiomycete and a rice bran extracts solution-enzyme reaction mixture can give rise to substances having high physiological activities.

(C-1) Basidiomycete Culture Solution

The basidiomycete culture solution used in the process of producing the physiologically active substances of the present invention is a culture solution obtained by culturing a basidiomycete in a liquid medium suitable for its growth.

Examples of carbon source in the liquid medium include glucose, sucrose, maltose, saccharose, high grade white sugar, black sugar, molasses, waste molasses, malt extracts and so forth.

Examples of nitrogen source includes, meat extracts, peptone, gluten meal, soybean powder, dry yeast, yeast extracts, ammonium sulfate, ammonium tartrate, urea and so forth. In addition, inorganic salts such as sodium salts, magnesium salts, manganese salts, iron salts, calcium salts and phosphoric acid salts, vitamins such as inositol, vitamin B1 hydrochloride, L-asparagine, and biotin may optionally be added.

The composition of preferred liquid medium may vary depending on the strain of basidiomycete but may be comprised, for example, by malt extracts (1 to 5%), yeast extracts (0.1 to 0.5%), and ammonium tartrate (0.1 to 0.4%).

Examples of the basidiomycete used in the present invention include *Lentinum edodes, Agaricus bisporus, Grifola frondosa, Phoriota nameko, Pleurotus ostreatus, Flam-*

*mulina velutipes, Ganoderma luriduim, Auricularia auricura, Ganoderma applanalum, coriollis lucidum, Grifola umbellate, Shizophyllum commune, Volvariella volvaceae* and so forth. Particularly preferred are *Lentinus edodes* and *Grifola frondosa.*

The culture is performed according to aeration culture for ordinary medium temperature microbes, i.e., at pH 2 to 6 and at a temperature of 10 to 45° C., preferably 15 to 30° C. The culture time may vary depending on the type and amount of the microbe and usually it lasts for 4 to 20 days, preferably 6 to 12 days.

After the cultivation, solid-liquid separation is performed and the liquid components are used for subsequent reaction with the rice bran extracts solution-enzyme reaction mixture.

(C-2) Rice Bran Extracts Solution-Enzyme Reaction Mixture

The rice bran extracts solution is an aqueous solution obtained by stirring a certain amount of rice bran in an equivalent amount or more (for example, 2 to 10 folds) of hot water. On this occasion, it is preferred to use pressurized water at about 105 to about 130° C. Subsequently, rice bran is reacted by addition of an enzyme agent and subjected to solid-liquid separation using a decanter or the like to obtain a rice bran extracts solution-enzyme reaction mixture.

As the enzyme agent, a carbohydrate hydrolase such as α-amylase, cellulase or pectinase may be used alone or in combination of two or more of them. A proteolytic enzyme such as protease may be used in combination. The enzyme reaction is performed under conditions where the enzyme activity is not damaged, that is, at about 40° C. or higher and about 90° C. or lower, preferably about 40 to about 70° C., for about 1 to about 24 hours, preferably about 3 to about 12 hours.

(C-3) Reaction Between Basidiomycete Culture Medium and Rice Bran Extracts Solution-Enzyme Reaction Mixture The reaction between a basidiomycete culture and a rice bran extracts solution-enzyme reaction mixture is carried out preferably at 40° C. or higher and 90° C. or lower and more preferably 40 to 70° C. Usually, the both reactants are mixed and allowed to react for 8 to 24 hours. Then, the whole liquid is heated at 120° C. or higher under pressure to inactivate the enzymes and the like in the liquid and optionally separated and purified.

The separation and purification methods are not particularly limited and various separation methods may be applied. From the viewpoint of economy, a gas chromatography method is preferable.

In the case of conventional basidiomycete-derived physiologically active substances, selections of constitution of column and an eluent have been determined in a trial-and-error manner by way of color reactions or biological examinations. The color reactions allow ambiguous interpretation or biological examinations that takes a long time for judgment since few data on the chemical structure of the objective compound have been available. In contrast, in the present invention, the chemical structure of the objective physiologically active substance is already clarified and selection of the constitution of column and eluent can be easily made according to the hydrophilicity, molecular weight and other properties of the substance based on the structural formula thereof. Further, objective fractions can be quickly distinguished by using the following spectroscopic characteristics as indices.

(1) The $^1$H-NMR spectrum shows a peak attributable to the methyl-hydrogen of methyl ketone and AB system peaks attributable to the hydrogen atoms at the 4,5-positions of a 2,3-di-substituted furan ring.

(2) The $^{13}$C-NMR spectrum shows 6 peaks attributable to glucopyranose and 6 peaks attributable to isomaltose.

The peak attributable to the methyl-hydrogen of methyl ketone is found near δ2.48 (3H, s). The peaks attributable to the hydrogen atoms at the 4,5-positions of 2,3-di-substituted furan ring are recognized as AB system near δ6.78 and δ7.67 (both values were measured in deuterated methanol).

Besides, reference may be made to infrared absorptions. at 3000 to 3700 cm$^{-1}$ (hydroxyl group), 1660 cm$^{-1}$ (conjugated carbonyl group) and 1584 cm$^{-1}$ (double bond).

(E) Uses

The physiologically active substance of the present invention uses safe materials that have conventionally been provided as esculent materials (rice bran extracts solution and edible basidiomycete culture medium) and there are little possibilities of being contaminated with toxic side products. Therefore, the physiologically active substance of the present invention itself can be widely utilized as health food, medicine, reinforcing food, feedstuff and so forth.

When it is used for these uses, for example, as a health food, the physiologically active substance obtained in the above process (C-3) is concentrated or purified depending on the purpose. The physiologically active substance of the present invention is relatively stable to heat. However, it is preferred that lyophilization be used for the concentration and drying. The physiologically active substance of the present invention may be formulated using a food additive, an excipient or the like.

The medicinal uses may include medicines for humans and medicines for animals. When the inventive products are administered as a medicine, the physiologically active substances of the formula (I) above may be used as they are. or as a medical composition obtained by adding it to a nontoxic, inert carrier that is pharmaceutically acceptable. As the carrier, solid, semi-solid or liquid diluents, filler and auxiliaries for other formulations and so forth are used.

The medicines may be administered by intravenous administration, oral administration, tissue administration, topical administration (percutaneous administration, etc.) or perrectal administration. The formulation may be of any form that is suitable for the above administration methods.

Uses as the feedstuff includes feedstuff for livestock and poultry such as cows, pigs, hens and sheep, feedstuff for fish culture for fish or crustaceans, and feedstuff for pets such as dogs, cats and others.

In recent years, the effects of minimizing the problems caused by use of large amounts of antibiotics, which attention has been paid to in the field of animal husbandry, can be expected. The above physiologically active substances may be orally administered alone but it is preferable to use them together with various glycosides, proteins, lipids, fibers, vitamins, and minerals and so forth as feedstuff in the form of dusts or pellets. The types of lipids and fibers are not particularly limited but any substance that can be used as feedstuff, such as fish, meat bone powder, soybean meal, alfalfa meal, and bran.

BEST MODE FOR CARRYING OUT THE INVENTION

Hereinafter, the physiologically active substance of the present invention will be explained in detail by production examples and physiological activity assay results.

The physiological activity assays were performed by forcibly administering 1 g/kg of a sample to 6-week age male C57/BL6 mice for 1 week by oral route. Spleen cells and peritoneal exudate cells (PEC) were collected after sacrificing the animals. They were cultivated and assayed TNF-α, IFN-γ, and IL-2.

a) Cultivation of Spleen Cells

The collected mouse spleen was homogenized in DMEM medium and the homogenate was centrifuged at 4° C. (1,000 rpm, 5 minutes) To this was added ASK lysis buffer and the mixture was incubated (37° C., 3 minutes) in order to remove erythrocytes, followed by centrifugation (1,000 rpm, 5 minutes). To the spleen cells thus collected was added ConA at a final concentration of 10 μg/ml and cultivated in a microplate. After 15 hours, the culture supernatant was collected for assaying TNF-α, IFN-γ, and IL-2.

b) PEC Cultivation

PEC (peritoneal exudate cells) collected from mouse abdominal cavity with physiological saline were centrifuged, (1,000 rpm, 10 minutes) to collect cells, which were used as macrophages. To the macrophages LPS (lipopoly saccharide) was added at a final concentration of 100 ng/ml and the cells were cultivated. After 4 hours, TNF-α, IFN-γ, and IL-2 in the culture supernatant were assayed.

For both a) and b) above, a kit for assaying cytokine (Wako Pure Chemical Industries, Ltd.) was used.

EXAMPLE 1

Confirmation of Physiological Active Substance

In a liquid medium having the composition containing malt extracts (2%), yeast extracts (0.25%) and ammonium tartrate (0.2%), Shiitake mushroom (*Lentinus edodes*) was cultivated with aeration at 24° C. for 10 days to prepare a basidiomycete culture solution.

On the other hand, rice bran was dispersed in 5-fold (mass) water and stirred at a liquid temperature of 120° C. for 20 minutes to effect extraction. Thereafter, an enzyme agent composed of α-amylase and pectinase was added to thereto, and reaction followed at 60° C. for 120 minutes. Then, the reaction mixture was subjected to solid-liquid separation and the liquid portion was recovered to prepare a rice bran extracts solution-enzyme reaction mixture.

Neither the basidiomycete culture solution nor rice bran extracts solution-enzyme reaction mixture exhibited any physiological activity.

On the other hand, the basidiomycete culture solution and the rice bran extracts solution-enzyme reaction mixture obtained by the above procedures were mixed together and the resultant mixture was stirred at 60° C. for 20 hours for reaction. Then, the whole liquid was heated at 120° C. or higher for 20 minutes to inactivate the enzymes and so forth in the liquid, the reaction mixture was concentrated, and 80 ml of the reaction mixture (moisture content: 75%) was eluted with methanol through a 500-ml DIAION HP-20 column. As a result, physiological activity was observed in the eluate. Therefore, this procedure was repeated twice to obtain a brown fraction (5.6 g).

Further, the fraction was subjected to detection of physiologically active components by various column chromatographic analyses. That is, the fraction was subjected to silica gel chromatography (Kiesel, produced by Merck & Co., Inc., 125-mesh, 50 g) and subsequently to ODS based reversed phase gel column chromatography (about 100 ml in volume) to obtain white powdery physiologically active component (40 mg) The obtained substance had the following physical properties.

(i) Mass Spectrometry (Secondary Ion Mass Spectrometry (SIMS))

Negative ionization measurement showed a molecular ion peak at m/z: 287 and positive ionization measurement showed a molecular ion peak of m/z: 289. As a result, the molecular weight of the present compound was found to be 288. Further, the above results together with the results of high-resolution mass spectrometry of these ion peaks suggested that the molecular formula of the compound would be $C_{12}H_{16}O_8$ (degree of unsaturation: 5).

(ii) IR Spectrum

Absorptions were observed at 3000 to 3700 $cm^{-1}$ attributable to a hydroxyl group, at 1660 $cm^{-1}$ attributable to a conjugated carbonyl group and at 1584 $cm^{-1}$ attributable to a double bond.

(iii) $^1$H-NMR Spectrum (in Deuterated Methanol, 270 MHz)

There were observed signals at δ2.48 (3H, s) attributable to methyl ketone and at δ3.4–5.6 attributable to α-D-glucopyranose ring, as well as peaks at δ6.78 and δ7.67 attributable to an AB system having a coupling constant of 1.9 Hz.

(iv) $^{13}$C-NMR Spectrum (in Deuterated Methanol, 67.5 MHz, DEPT measuring method)

Twelve (12) signals were observed. That is, besides a group of six signals attributable to α-D-glucopyranose ring, six signals attributable to aglycon moieties were observed at δ27.4 (primary), δ105.9 and 139.3 (each being tertiary), δ148.5, 154.3, and 187.4 (each being quaternary).

The low magnetic field AB system in $^1$H-NMR is considered to be characteristic to the hydrogen signal at the 4,5-positions of 2,3-di-substituted furan ring in view of its coupling constant being 1.9 Hz. The degree of unsaturation of the molecular formula being 5 corresponds to one pyranose ring, two double bonds, one carbonyl group and one furan ring. From the above information, the obtained substance was confirmed to be a novel substance (2-acetyl-3-hydroxyfuran 3-O-α-D-glucopyranoside, hereinafter referred to as "substance A") represented by the formula below.

Confirmation of Production Process of Substance A:

In the same manner as described above, the rise and fall of the substance A that would exist in the basidiomycete culture solution, rice bran extracts solution-enzyme reaction mixture, the reaction mixture between the above two and so forth were followed up. As a result, it was confirmed that the substance A was produced only in the reaction mixture between the basidiomycete culture solution and the rice bran extracts solution-enzyme reaction mixture. No substance A existed in the basidiomycete culture solution or in the rice bran extracts solution-enzyme reaction mixture. It revealed that the substance A is produced only by reaction between the two.

EXAMPLE 2

Chemical Synthesis of Substance A

In accordance with the example of reaction in which galactosylisomaltol is chemically derived from lactose as a starting material as disclosed in J. Bartulin et al., J. Heterocycle Chem., 29, 1017 (1992), "Syntheses of 2-Acetyl-3-hydroxy-1-n-propylpyrrole from Isomaltol and 1-n-Alkyl-3-hydroxy-2-methyl-4-pyridones form Maltol," substance A was chemically derived using maltose in place of lactose.

(a) Chemical Derivation Reaction

In a 50-ml eggplant type flask, 3.60 g (0.01 mol) of maltose monohydrate was weighed and 3.0 ml of anhydrous ethanol was added thereto. The mixture was stirred vigorously with a stirrer contained therein to disperse maltose. On this occasion, the state in which an undissolved portion of the maltose monohydrate was stirred and uniformly dispersed throughout the anhydrous ethanol without localization was maintained. While vigorously stirring the mixture, 1.0 ml of piperidine was added thereto and uniformly mixed therewith. Then, 0.44 ml of acetic acid was slowly dripped over about 15 minutes using a measuring pipette. In a silicone oil bath adjusted to 78° C., the eggplant type flask equipped with a water stream condenser was placed and reaction is allowed to proceed. When the heat distributed throughout the flask throughout and boiling started in portions thereof, about 0.5 ml of triethylamine was added. After the placement of the flask, maltose monohydrate began to be dissolved due to the heat and accordingly the solution turned from yellow to brown. After about 12 hours, the same volume as above of triethylamine was added to keep the liquid basic. After 24 hours, the flask was taken out from the refluxing apparatus and the temperature of the flask was returned to room temperature before purification operation could be proceeded. Then the reaction product was intense brown tar-like substance in nature.

The reaction product was subjected to TLC analysis using a plate with a solvent (chloroform/methanol/water (65:25:4) mixed solution). As a result, a spot having an absorption when irradiated by ultraviolet rays with a main wavelength of 254 nm was observed at the same Rf value (about 0.5) as substance A. When it is sprayed with an anisaldehyde-sulfuric acid coloring reagent and heated, the spot turned yellow and further intense blue.

(b) Purification (b-1) Crude Purification with LH-20 Gel

A necessary volume of LH-20 gel was preliminarily passed through methanol/water (1:2) to equilibrate it and the reaction mixture mixed with a minimum amount of the same solvent was charged thereto. The reaction mixture was developed and fractionated with the same solvent and the fractions containing the objective compound were combined. The fraction obtained was evaporated and concentrated to dryness to obtain a brown oily substance (0.49 g).

(b-2) Purification by Silica Gel Column Chromatography

Sample was charged and developed in a column prepared using silica gel of about 200 mesh in an amount of 20 to 30 times the weight of the sample. Chromatography was performed again with water-saturated ethyl acetate/methanol (3:1) and then rechlomatographed with a chloroform/methanol/water mixed solution (a saturation amount of water was added to 4:1 chloroform/methanol). The purified fraction was evaporated and concentrated to dryness to obtain a yellow resinous substance (0.49 g).

(b-3) Crystallization

The yellow resinous substance was crystallized from methanol to obtain colorless needle crystals (0.37 g).

The substance thus obtained showed the same behavior on chromatography and NMR spectrum as those of the substance A.

EXAMPLE 3

Existence of the substance A in the reaction mixture between the basidiomycete culture solution and the rice bran extracts solution-enzyme reaction mixture suggested the possibility that the physiologically active substance in the basidiomycete culture solution could comprise glucosides having isomaltol structures at the reducing terminals thereof with sugar linkages of different lengths.

Accordingly, the basidiomycete culture solution and the rice bran extracts solution-enzyme reaction mixture were prepared by the same procedures as in Example 1 and reacted at 60° C. for 20 hours by stirring. Then the entire reaction mixture was heated to 120° C. or higher for 20 minutes to inactivate the enzymes and so forth in the reaction mixture. Thereafter, effective components having higher molecular weights were searched using the following spectroscopic characteristics as indices.

(a) $^1$H-NMR spectrum shows a peak attributable to methyl hydrogen of methyl ketone and an AB system peak attributable to hydrogen atoms at the 4,5-positions of a 2,3-di-substituted furan ring, and (b) $^{13}$C-NMR spectrum shows 6 peaks attributable to glucopyranose and 6 peaks attributable to isomaltol.

More particularly, in a column for chromatography (DIAION HP-20, volume: about 500 ml) was charged 80 ml (20 g as solids) of the above concentrate and then eluted with 1.5 liters of water. The eluate was dried under vacuum to obtain 18 g of powder. This fraction was dissolved in 45 ml of water and the obtained solution was dispensed in two centrifuging tubes each in an amount of 22.5 ml. While stirring each solution, a 4-fold volume, i.e., 90 ml of ethanol was slowly dripped to each solution, which then was centrifuged at 3,000 rpm for 10 minutes. The obtained supernatants were combined, concentrated and freeze-dried to obtain powder (12 g). The powder was dissolved in 50 ml of water and the solution was purified through column chromatography (DOWEX 50W-X8 (H$^+$ type)). 10.8 g of the obtained water-eluted portion was further purified through column chromatography (AMBERLITE IRA-400 (CO$_3^{2-}$ type)), concentrated and freeze-dried to obtain 8.64 g of water-eluted powder. This was further purified through column chromatography (SEPHADEX G-15) to obtain 2.16 g of a component that satisfies the requirements (a) and (b) above.

The obtained substance had the following physical properties.

(i) $^1$H-NMR Spectrum (in Deuterated Water, 270 MHz)

Weak, broad proton signals presumed to be attributable to AB system on a furan ring were detected at $\delta 6.85$ and $\delta 7.35$.

(iv) $^{13}$C-NMR Spectrum (in Deuterated Water)

Weak signals presumed to be attributable to isomaltol were observed at δ26 (—C(O)CH$_3$), 111 (C-4), 141 (C-3), 145 (C-5), and 188 (—C (O)—)

From the above, the obtained substance is presumed to have a structure represented by the following formula:

This substance (hereinafter referred to as "substance B") is a mixture of compounds between isomaltol and oligosaccharides (composed of D-glucose molecules with different degrees of polymerization) (in the above general formula (II), n=2 to 20). It has an average molecular weight of 850 as obtained based on a calibration curve prepared in advance. The oligosaccharides include mainly glucose molecules with α-1,4 glycoside bonds and partially those with α-1,6 bonds or other bonds.

In the same manner as in Example 1 (2), the rise and fall of the substance B that would exist in the basidiomycete culture solution, rice bran extracts solution-enzyme reaction mixture, the reaction mixture between the above two and so forth were followed up. As a result, it was confirmed that the substance B was produced only in the reaction mixture between the basidiomycete culture solution and the rice bran extracts solution-enzyme reaction mixture. No substance B existed in the basidiomycete culture solution or in the rice bran extracts solution-enzyme reaction mixture. It revealed that the substance B is not produced before the both of them could be reacted. As will be shown in Example 4, it was confirmed that the substance B has a physiological activity.

EXAMPLE 4

The physiological activities of the substance A obtained in Example 1 and the substance B obtained in Example 3 were compared.

Figure 1:
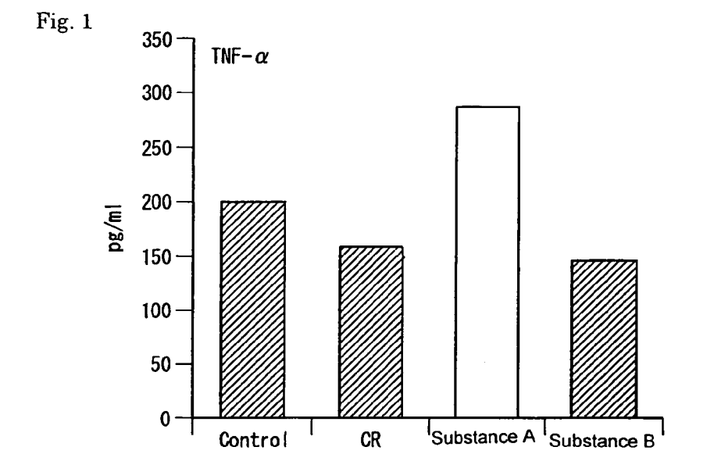
FIG. 1 is a graph showing the results of measurement of TNF-α concentration in the supernatant of spleen cell culture after administration of the substance A in the present invention (compound of formula (III)), substance B in the present invention (compound of formula (I)), and crude product according to the present invention (CR).
Figure 2:
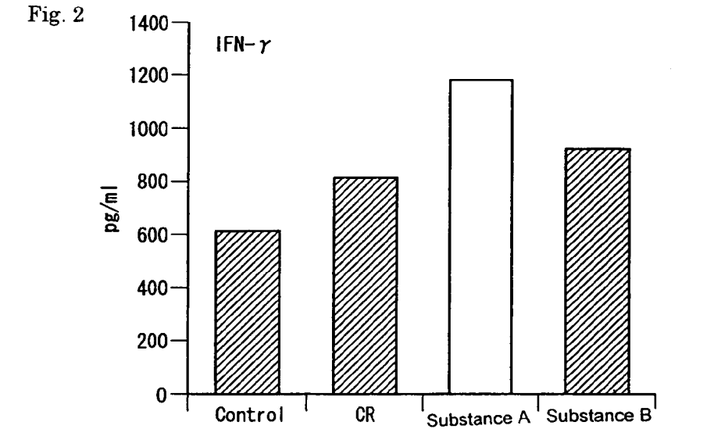
FIG. 2 is a graph showing the results of measurement of IFN-α concentration in the supernatant of spleen cell culture after administration of the inventive substance A in the present invention (compound of formula (III)), inventive substance B in the present invention (compound of formula (I)), and crude product according to the present invention (CR).
Figure 3:
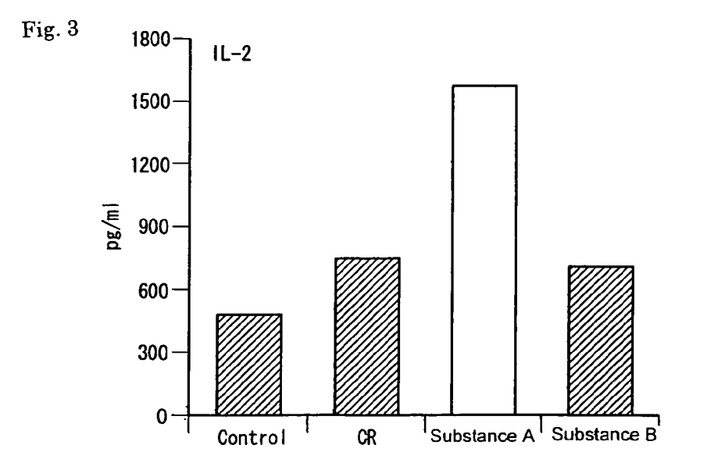
FIG. 3 is a graph showing the results of measurement of IL-2 concentration in the supernatant of spleen cell culture after administration of the inventive substance A in the present invention (compound of formula (III)), inventive substance B in the present invention (compound of formula (I) and crude product according to the present invention (CR).
Figure 4:
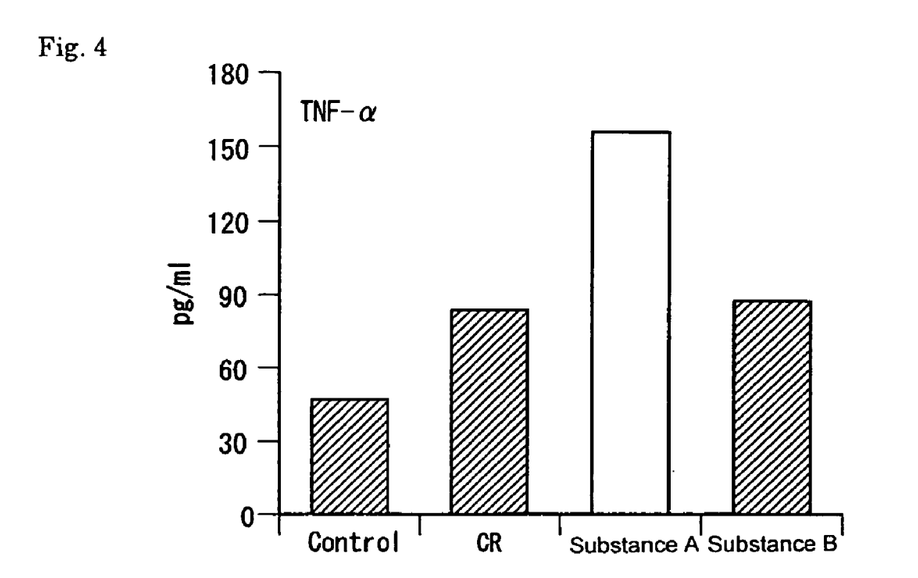
FIG. 4 is a graph showing the results of measurement of TNF-α concentration in the supernatant of macrophage culture after administration of substance A in the present invention(compound of formula (III)), substance B in the present invention (compound of formula (I)), and crude product according to the present invention (CR).
Figure 5:
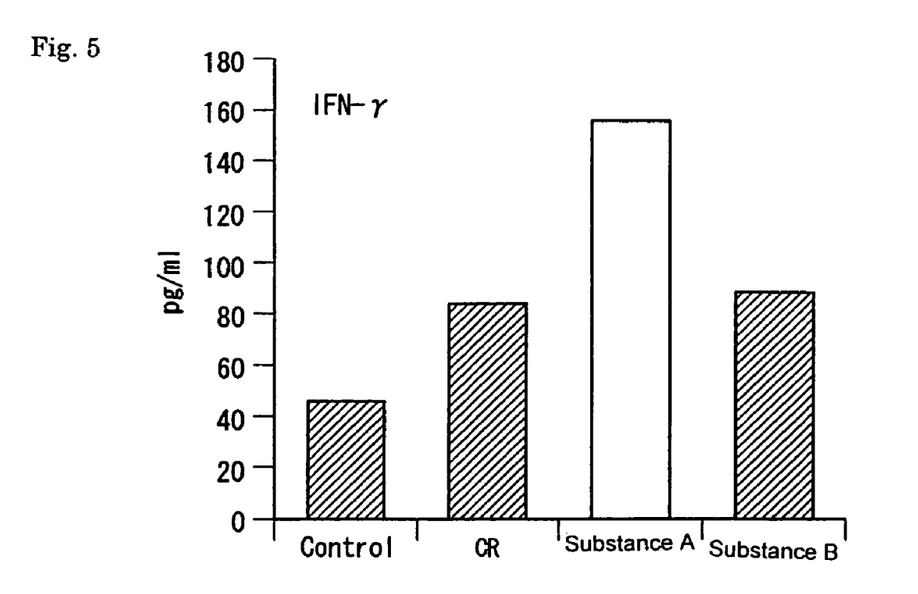
FIG. 5 is a graph showing the results of measurement of IFN-γ concentration in the supernatant of macrophage culture after administration of substance A in the present invention (compound of formula (III)), substance B in the present invention(compound of formula (I)), and crude product according to the present invention (CR).

FIGS. 1 to 3 illustrate the results of measurement of concentrations of cytokines (TNF-α, IFN-γ and IL-2) in the supernatant of a spleen cell culture after administration of the substance A, substance B and crude concentrate. FIGS. 5 and 6 illustrate concentrations of cytokines (TNF-α and IFN-γ) in the supernatant of a macrophage culture. As a result, it revealed that the substance A showed considerable cytokine induction ability and the substance B showed superior effects in IFN-γ induction ability to the crude concentrate.

Concerning macrophage, it was observed that the substance A had high cytokine induction ability.

INDUSTRIAL APPLICABILITY

According to the present invention, it has been found that the component having a strong physiological activity contained in an amount of about 10% in the powder obtained by concentrating to dryness the reaction mixture between the basidiomycete culture solution and the rice bran extracts solution-enzyme. reaction mixture includes a series of compounds having a glucoside structure containing isomaltol as an aglycon. The compounds can be purified so as to have a high purity by a conventional means such as column chromatography using spectroscopic characteristics as indices.

Therefore, according to the present invention, it is possible to obtain a physiologically active substance with less contamination as compared with the conventional process for producing a physiologically active substance derived from a basidiomycete culture that uses a plant tissue material. The product is useful as food, feedstuff and medicine.

The glycosides that are the physiologically active substances of the present invention are not contained in the basidiomycete culture solutions. They are not produced merely by reacting rice bran extracts with an enzyme. The reaction between the basidiomycete culture solution and the rice bran extracts solution-enzyme reaction mixture is indispensable.

From the above, the substance A can be utilized as an index component for a process for producing medicines and for production management therefor. That is, when the substance A is detected, it may be presumed that the reaction between the basidiomycete and the rice bran extracts solution-enzyme reaction mixture is used in producing such products. The production amount of the substance A may vary depending on the method and conditions for cultivating a basidiomycete, conditions for preparing rice bran extracts solution-enzyme reaction mixture (kind of enzyme used, conditions of enzyme reaction and so forth), conditions for the reaction between the two. However, production management for novel substances having a physiological activity of the present invention can be realized using the substance A as an index.

The invention claimed is:

1. A method for producing a glucoside, having a physiological activity, represented by formula (I):

wherein Sug represents a glucose residue or a sugar linkage composed of two or more glucose units, comprising reacting a culture solution obtained by culturing a basidiomycete with a reaction mixture obtained by reaction between a rice bran extracts solution and an enzyme.

2. A method for producing a glucoside, having a physiological activity, represented by formula (I):

wherein Sug represents a glucose residue or a sugar linkage composed of two or more glucose units, comprising reacting a culture solution obtained by culturing a basidiomycete with a reaction mixture obtained by reaction between a rice bran extracts solution and an enzyme, and isolating the glucoside by column chromatography using as an index a component showing (1) a peak attributable to methyl hydrogen of methyl ketone by $^1$H-NMR spectrum and a peak attributable to hydrogen atoms at the 4,5-positions of a 2,3-di-substituted furan ring characteristic of AB system, and (2) 6 peaks attributable to glucopyranose and 6 peaks attributable to isomaltol by $^{13}$C-NMR.

* * * * *